US00PP37123P3

(12) United States Plant Patent
Gereda Cornejo et al.

(10) Patent No.: US PP37,123 P3
(45) Date of Patent: Dec. 9, 2025

(54) BLUEBERRY PLANT NAMED 'IBUGA002'

(50) Latin Name: *Vaccinium corymbosum*
Varietal Denomination: IBUGA002

(71) Applicant: BLOOM FRESH INTERNATIONAL LIMITED, London (GB)

(72) Inventors: Carlos Alberto Gereda Cornejo, Lima (PE); D. Scott Nesmith, Griffin (GE)

(73) Assignee: Bloom Fresh International Limited, London (GB)

( * ) Notice: Subject to any disclaimer, the term of this patent is extended or adjusted under 35 U.S.C. 154(b) by 0 days.

(21) Appl. No.: 18/767,671

(22) Filed: Jul. 9, 2024

(65) Prior Publication Data

US 2025/0063959 P1 Feb. 20, 2025

(30) Foreign Application Priority Data

Aug. 17, 2023 (PE) ..... 2381-2023/DIN
Feb. 7, 2024 (QZ) ..... PBR 2024/0288

(51) Int. Cl.
*A01H 5/02* (2018.01)
*A01H 6/36* (2018.01)
*A01H 6/82* (2018.01)

(52) U.S. Cl.
USPC ..... Plt./157
CPC ..... *A01H 6/368* (2018.05)

(58) Field of Classification Search
USPC ..... Plt./156, 157
See application file for complete search history.

(56) References Cited

U.S. PATENT DOCUMENTS

PP31,863 P2 6/2020 NeSmith
PP33,755 P2 12/2021 NeSmith
PP34,180 P2 5/2022 NeSmith

*Primary Examiner* — Karen M Redden
(74) *Attorney, Agent, or Firm* — Panitch Schwarze Belisario & Nadel LLP; Stephany G. Small; Travis W. Bliss

(57) ABSTRACT

The new blueberry plant variety 'IBUGA002' is provided. 'IBUGA002' is a commercial variety that does not require chilling hours. The variety is produced from open pollination of the 'TH-909' variety (not patented). 'IBUGA002' displays a semi-erect to prostrate plant with strong vigor, provides early berry ripening, displays clustered inflorescence, and exhibits large fruit that are firm.

5 Drawing Sheets

Latin name of the genus and species:
Genus—*Vaccinium.*
Species—*corymbosum.*
Variety denomination: The new blueberry plant claimed is of the variety denominated 'IBUGA002'.

CROSS REFERENCE TO RELATED APPLICATIONS

This application claims priority to Plant Breeders' Right Application No. 2024/0288, which was filed at Community Plant Variety Office in the European Union on Feb. 7, 2024, and to Plant Breeders' Right Application No. 2381-2023/DIN filed in Peru on Aug. 17, 2023, the contents of which are hereby incorporated by reference for all purposes.

Copending U.S. Plant patent application Ser. No. 18/767,637 was filed on Jul. 9, 2024, and is directed to a new blueberry plant variety 'IBUGA001', which was developed by the same breeding program as the new variety of the instant application.

BACKGROUND OF THE INVENTION

The present invention relates to the discovery of a new and distinct cultivar of southern highbush blueberry (*Vaccinium corymbosum*) plant, referred to as 'IBUGA002' as herein described and illustrated.

Pedigree and History: The new blueberry plants originated from an open pollination of the 'TH-909' variety (not patented) in Griffin, Georgia in 2015. The progeny of this open pollination were germinated in 2016, planted and growing in Huacho, Peru since 2017, and planted and growing in Lunahaná, Peru and Cayaltí, Peru from 2022, for further research evaluation. The new variety 'IBUGA002' was selected in Huacho, Lima, Peru in 2019.

'IBUGA002' has been found to undergo in vitro asexual propagation. Asexual propagation techniques, such as in vitro, have shown that the characteristics of the new variety are homogenous, stable, and strictly transmissible by such asexual propagation from one generation to another. Accordingly, the new variety undergoes asexual propagation in a true-to-type manner.

SUMMARY OF THE INVENTION

The following characteristics of the new cultivar have been repeatedly observed and are determined to be the unique characteristics of the new blueberry plant variety 'IBUGA002':

(a) displays strong vigor,
(b) exhibits early berry ripening, and
(c) provides firm, large fruit.

The new variety of the present invention can readily be distinguished from its ancestors. More specifically, the 'TH-909' variety (i.e., the seed parent) has a chilling requirement of about 200 to 300 hours (see U.S. Plant Pat. No. 33,755), whereas the new variety does not have a chilling requirement. In addition, the 'IBUGA001' variety provides heavier berries that are less firm compared to berries of the new variety. The new variety can also be distinguished from other similar varieties that are commercially available. For instance, the new variety of the present invention is mid-season and the fruits begin to ripen earlier than the 'Biloxi' variety (not patented) and the 'TH-1996' variety (U.S. Plant Pat. No. 34,180) and much earlier than the 'TH-1125' variety (U.S. Plant Pat. No. 31,863) on the central coast of Peru. In addition, the new variety is a semi-erect to prostrate plant, compared to 'Biloxi' and 'TH-1996', which are both bushy and taller, and to 'TH-1125', which is erect. The new variety produces inflorescence that is clustered and well distributed, with looser berries observed at harvest, unlike 'Biloxi' and 'TH-1125', which have tighter berries. Also, 'IBUGA002' has a performance productive superior to 'Biloxi' and 'TH-1996'. 'Biloxi', 'TH-1996', and 'TH-1125' each require chilling hours, compared to the new variety that does not require chilling hours. Further, 'IBUGA002' produces well as an evergreen or continuously producing variety.

Additional comparisons are found in Table 1, which includes a three-year average rating of the fruit characteristics of 'IBUGA002', 'IBUGA001', 'TH-1996', 'TH-1125', and 'Biloxi', from 2019-2021, in test plots in Huacho, Lima, Peru. Rating scales are based on a score of 1-10, with 1 being the least desirable and 10 being the most desirable. A value of 6-7 is generally considered the minimum acceptable rating for a commercial cultivar.

TABLE 1

| Characteristic | 'IBUGA002' | 'IBUGA001' | 'TH-1996' | 'TH-1125' | 'Biloxi' |
|---|---|---|---|---|---|
| Berry size | 8.4 | 8.5 | 8.5 | 7.5 | 6.0 |
| Berry scar | 8.0 | 8.5 | 8.0 | 9.0 | 7.5 |
| Berry color | 7.5 | 8.0 | 7.0 | 8.5 | 6.5 |
| Berry firmness | 9.0 | 7.0 | 8.0 | 9.5 | 7.0 |
| Berry flavor | 8.5 | 7.5 | 8.0 | 8.0 | 7.5 |
| Harvest | 9.0 | 9.0 | 7.0 | 7.0 | 6.0 |
| Plant vigor | 9.5 | 9.5 | 9.5 | 6.5 | 8.5 |
| 50% flowering date | May 5 | May 5 | May 6 | Aug 28 | May 20 |
| 50% ripening date | Aug 4 | July 28 | Aug 4 | Nov 28 | Aug 20 |
| Fruit development period (days) | 91 | 91 | 90 | 90 | 92 |

Table 2 shows a two-year average weight, firmness, and brix degrees of berries of the new variety, 'IBUGA001', 'TH-1196', 'TH-1125', and 'Biloxi' varieties from 2019-2021 in test plots in Huacho, Lima, Peru.

TABLE 2

| Characteristic | 'IBUGA002' | 'IBUGA001' | 'TH-1996' | 'TH-1125' | 'Biloxi' |
|---|---|---|---|---|---|
| Berry weight (g/berry) | 3.1 | 3.7 | 3.3 | 2.9 | 1.8 |
| Brix (%) | >12 | 11 | >12 | >11 | >12 |
| Firmness (g/mm) | 80 | 75 | 80 | 85 | 75 |

BRIEF DESCRIPTION OF THE DRAWINGS

The accompanying photographic illustration shows typical specimens in full color of the foliage, flowering, and fruit of plants of the new variety 'IBUGA002'. The colors are as nearly true as is reasonably possible in a color representation of this type. The colors in the photographs are as close as possible with the photographic and printing technology utilized. The color values cited in the detailed botanical description accurately describe the colors of the new blueberry. The photographs were taken of plants growing outdoors in Huacho, Lima, Peru under drip irrigation.

DETAILED BOTANICAL DESCRIPTION

Figure 1:
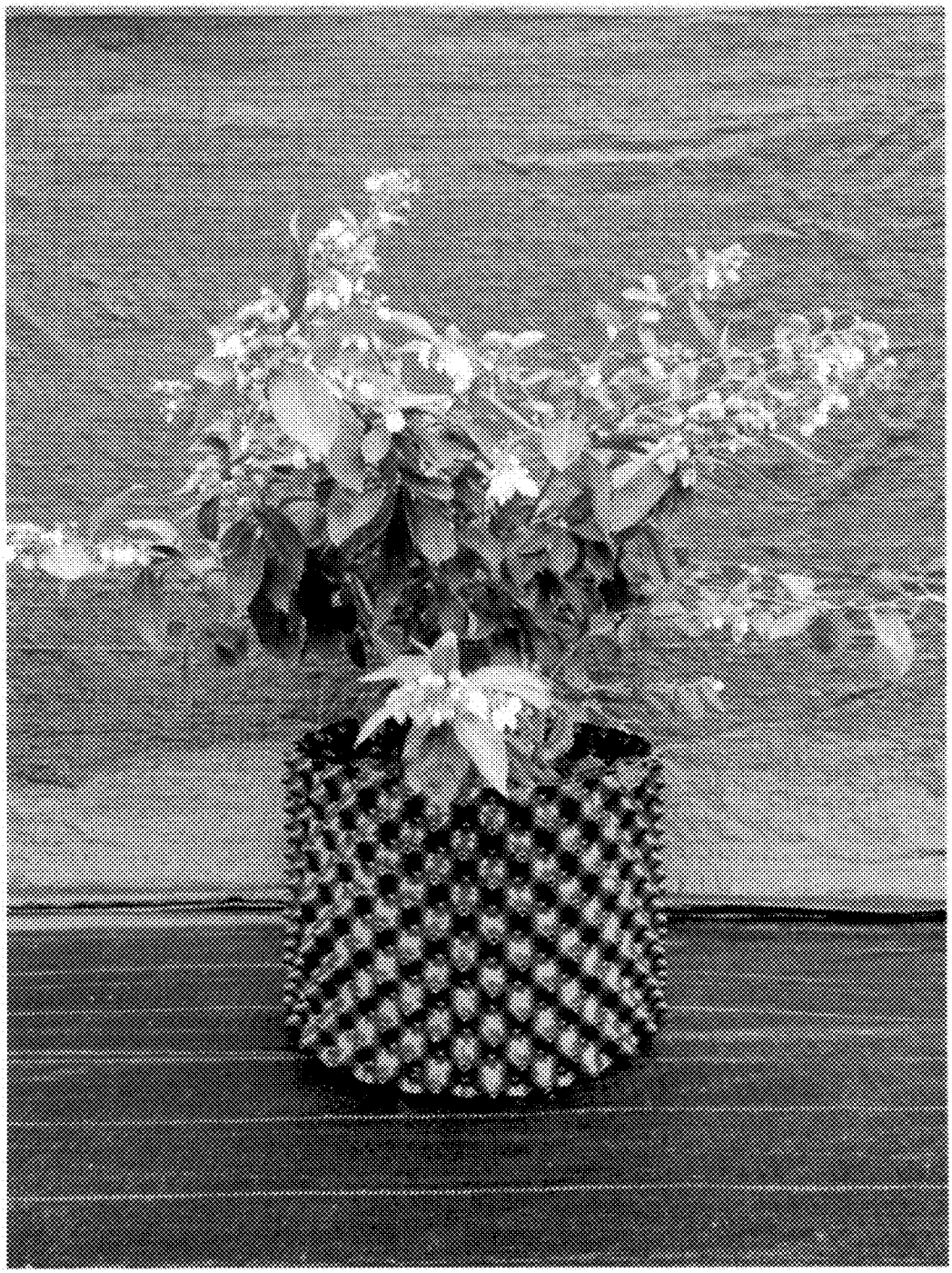
FIG. 1—depicts a plant of the new variety which was about 3 years old in flowering.
Figure 2:
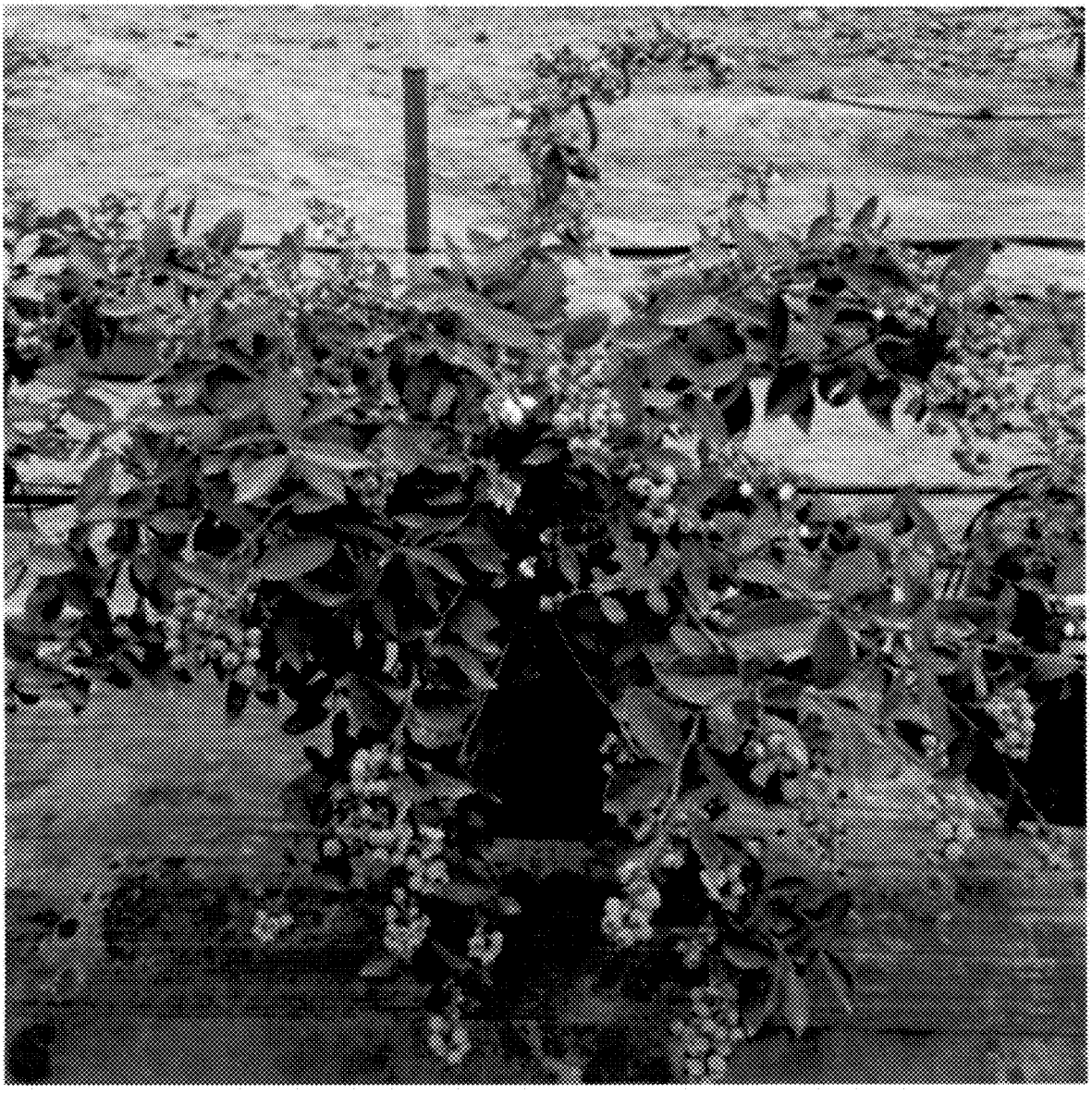
FIG. 2—depicts a plant of the new variety which was four years old during fruit ripening.
Figure 3:
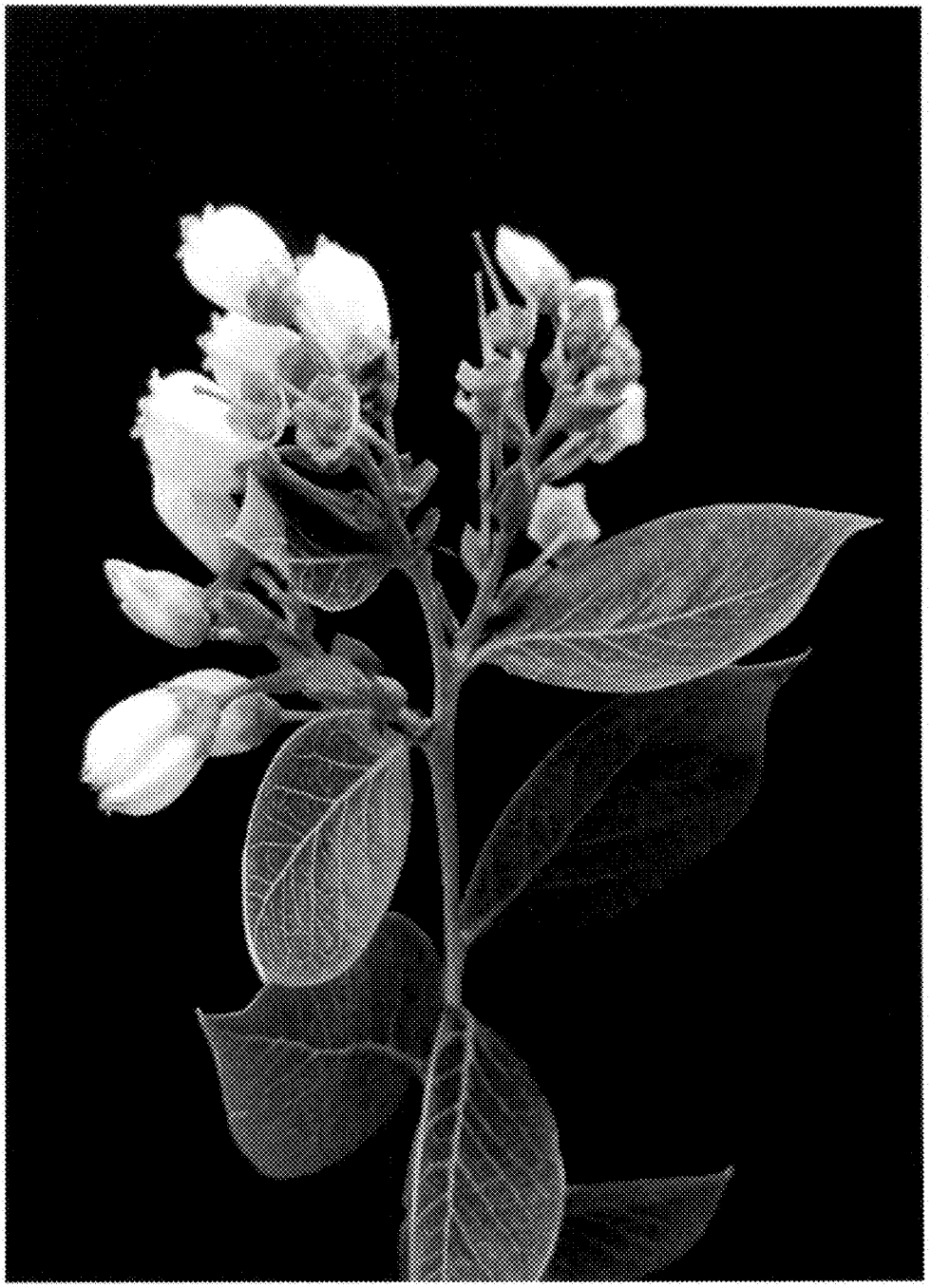
FIG. 3—depicts a close-up view of a flowered branch of the new variety.
Figure 4:
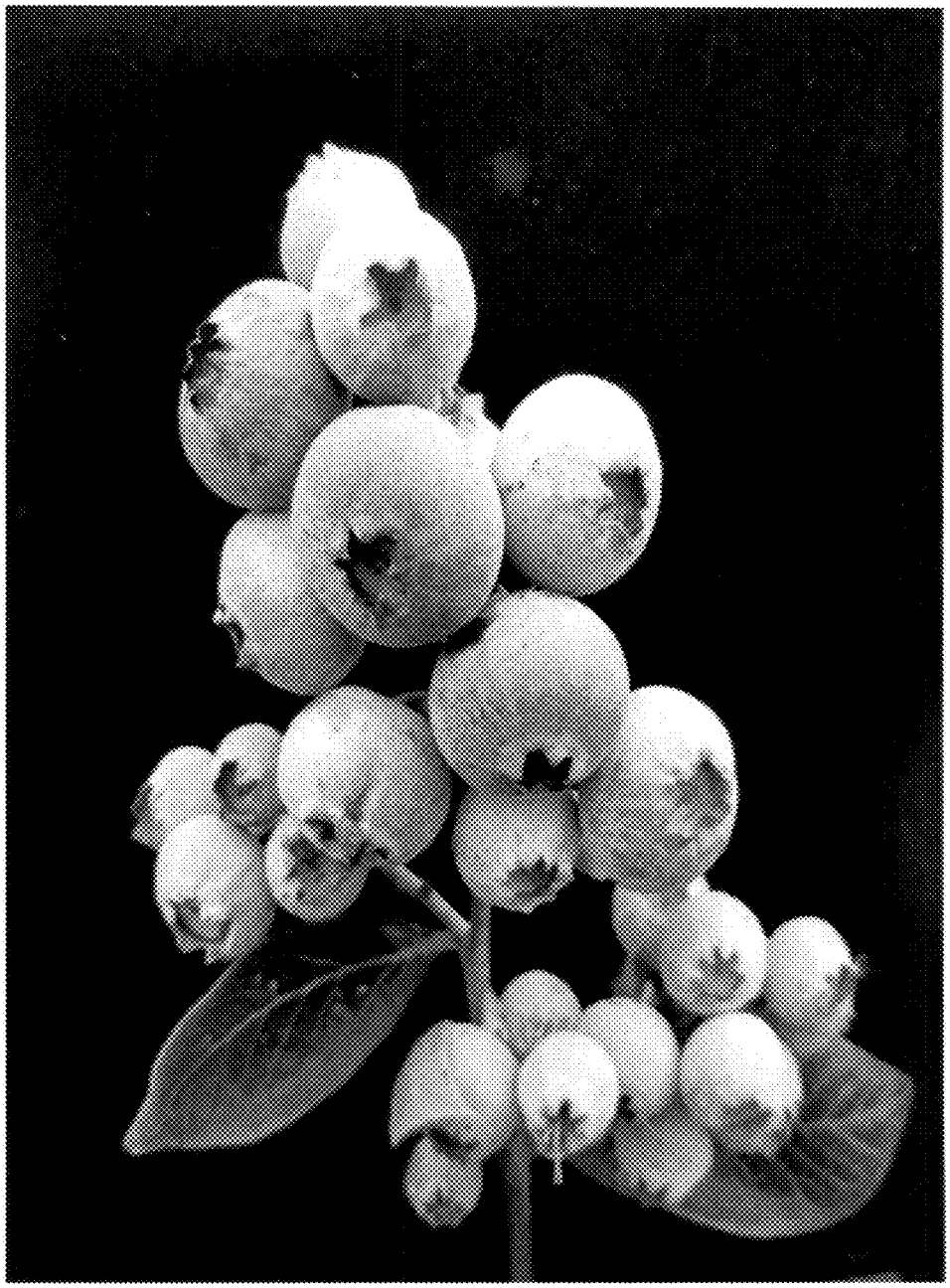
FIG. 4—depicts a close-up view of a branch with fruit of the new variety.
Figure 5:
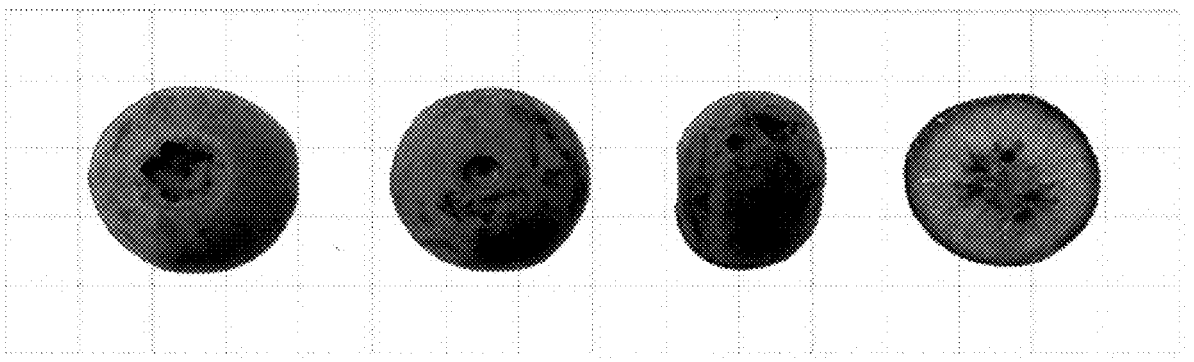
FIG. 5—depicts a close-up view of the fruit of the new variety; top, bottom, side view, and cross-section of the interior of the berry is shown. The grid is 1.0×1.0 cm.

The following detailed description sets forth the distinctive characteristics of 'IBUGA002'. The data which defines these characteristics was collected from the original plant of the new variety and from asexual reproductions of the original selection. Where dimensions, sizes, colors and other characteristics are indicated, it should be understood that such characteristics are approximations and averages established with the greatest possible precision. The descriptions presented here correspond largely to specimens grown in Huacho, Lima-Peru, conducted under drip irrigation. The plants were between 2 and 4 years old.

The chart used in the identification of colors is that of The Royal Horticultural Society (The R.H.S. Colour Chart, $5^{th}$ edition). The terminology which precedes reference to the chart has been added to indicate the corresponding color in more common terms and The R.H.S. Colour Chart designation used herein represents the closest color observed on the majority of the specified botanical feature. The new blueberry plant variety 'IBUGA002' has not been observed under all possible environmental conditions. The phenotype may vary somewhat with variations in environment and cultural practices such as temperature and light intensity without, however, any variance in genotype.

VARIETY

Classification:
*Family*.—Ericaceae.
*Genus*.—*Vaccinium*.
*Species*.—*Corymbosum*.
*Common name*.—Southern Highbush Blueberry.
Parentage:
*Female parent*.—'TH-909' (not patented).
*Male parent*.—Unknown, open pollination.

PLANT

General:
*Plant height*.—60.9 cm at 3 years old; plants grown under highly productive soil conditions have exceeded 1.0 m in height in 4 years of age.
*Plant diameter*.—Crown or base typically 15 to 25 cm; upper part of the plant canopy exceeds 91 cm by three to four years.
*Growth habit*.—Semi-erect growth with long stems that protrude and then settle to the sides, with more than 14 main canes (stems) that grow from the pruned branches of the previous year, with multiple branches of shoots that grow from those canes on the surface.
*Growth*.—Very vigorous.
*Productivity*.—Average harvest and yield, with an average of 4.0 to 5.0 kg of fruit per plant per year for plants 3 years old or older grown in well-fertilized soils with adequate irrigation.
*Endurance*.—Similar to other varieties of southern highbush berry plants; superior resistance to lack or excess of water or fertilization for short periods.
*Cooling*.—Zero cold hours needed; prone to producing evergreen leaves without requiring chilling hours when grown at lower latitudes.
*Foliation, production branches*.—Plants tend to break enough leaf buds simultaneously during or shortly after anthesis. Moderate number of twigs 10 to 15 cm long with typical internode lengths of 20 to 25 mm.
*Resistance to disease*.—No exceptional resistance or susceptibility to disease has been observed.

STEM

General:
*Color*.—Typically between N201D to 201C for the base of the canes; two-year cane transitions from 145A to 177B; 145A on current log.
*Diameter*.—Base of the main cane is 25 to 30 mm; cane after two years 10 to 15 mm; log of the current season 4 to 8 mm.

FOLIAGE

General:
*Leaf color* (*Top side*).—144A.
*Leaf color* (*Under side*).—144C.
*Leaf arrangement*.—Alternate, simple.
*Leaf shape*.—Elliptical.
*Undulation of margin*.—Almost smooth.
*Leaf venation*.—Reticular.
*Leaf length*.—60.5 to 70.5 mm.
*Leaf width*.—35.0 to 40.0 mm.
Petioles:
*Length*.—little.

FLOWERS

General:
*Time of* 50% *anthesis*.—May 5 in the northeast of Lima, Peru (three-year average).
*Flower shape*.—Urceolate.
*Flower bud density*.—Medium, with an average of 4 to 7 buds per fruit shoot.
*Flower fragrance*.—None.
Corolla:
*Color of inner and outer surfaces*.—NN155C.
*Length*.—10.0 to 13.0 mm.
*Width*.—7.0 to 8.0 mm.
*Aperture width*.—3.0 to 4.0 mm.
Inflorescence:
*Length of peduncle*.—8.0 to 10.0 mm.
*Color of peduncle*.—144C.
*Length of pedicel*.—10.0 to 12.0 mm.
*Color of pedicel*.—138B.
*Number of flowers per cluster*.—Typically 5 to 9.
Calyx (with sepals):
*Diameter*.—6.0 to 8.0 mm.
*Color of inner and outer surfaces* (*sepals*).—140D.
Stamen:
*Length*.—7.5 to 8.0 mm.
*Number per flower*.—10.
*Filament color*.—145D.
Style:
*Length*.—8.0 to 9.0 mm.
*Color*.—145B.
Pistil:
*Length*.—8.0 to 9.0 mm.
*Ovary color* (*exterior*).—138B.
Anther:
*Length*.—4.5 to 5.0 mm
*Number*.—10.
*Color*.—165B.
Pollen:
*Abundance*.—Medium to high.
*Color*.—158A.
*Self-compatibility*.—Moderate.

FRUIT

General:
*Time of* 50% *maturity*.—August in the Northeast of Lima (five-year average).
*Fruit development period*.—90 days average.
*Berry color*.—With wax is 98A to 98D; without wax is 103A.
*Berry surface wax abundance*.—Medium.
*Berry flesh color*.—150C.
*Berry weigh*.—First harvest is 3.2 to 3.7 g; second harvest is 2.4 to 2.9 g.
*Berry height from calyx to scar*.—12.0 to 15.0 mm.
*Berry diameter*.—17.0 to 21.0 mm.
*Berry shape*.—Half-disc shaped.
*Fruit stem scar*.—Small to medium, dry, with little or no tearing on the harvest.
*Flavor when ripe*.—High.
*Firmness when ripe*.—High.
*Storage quality*.—Very good.

*Suitability for mechanical harvesting*.—No information available.

*Uses*.—Fresh.

SEED

General:

*Seed abundance in fruit*.—Medium, 15 to 25 fully developed seeds per berry.

*Seed color*.—165B.

*Seed dry weight*.—44.0 mg per 100 seeds.

*Seed length*.—0.3 to 0.4 mm.

The invention claimed is:

1. A new and distinct variety of blueberry plant named 'IBUGA002', substantially as illustrated and described herein.

* * * * *